US012670976B2

(12) United States Patent
Nauwelaers et al.

(10) Patent No.: US 12,670,976 B2
(45) Date of Patent: Jun. 30, 2026

(54) SYSTEMS AND METHODS FOR IMPLEMENTING AN INDIVIDUALIZED DRUG DELIVERY PROFILE FOR A RECIPIENT OF A COCHLEAR IMPLANT SYSTEM

(71) Applicant: Advanced Bionics LLC, Valencia, CA (US)

(72) Inventors: Tim Nauwelaers, Hannover (DE); Stephan Geiger, Ventura, CA (US); Ersin Avci, Isernhagen (DE); Pierre Guillon, Stäfa (CH)

(73) Assignee: Advanced Bionics LLC, Valencia, CA (US)

( * ) Notice: Subject to any disclaimer, the term of this patent is extended or adjusted under 35 U.S.C. 154(b) by 0 days.

(21) Appl. No.: 18/754,965

(22) Filed: Jun. 26, 2024

(65) Prior Publication Data

US 2026/0004906 A1     Jan. 1, 2026

(51) Int. Cl.
*G16H 20/10*          (2018.01)
*A61N 1/05*          (2006.01)
(Continued)

(52) U.S. Cl.
CPC .......... *G16H 20/10* (2018.01); *A61N 1/0541* (2013.01); *A61N 1/36039* (2017.08); *A61N 1/372* (2013.01); *G16H 40/63* (2018.01)

(58) Field of Classification Search
CPC .... G16H 20/10; G16H 40/63; A61N 1/36039; A61N 1/0541; A61N 1/372
See application file for complete search history.

(56) References Cited

U.S. PATENT DOCUMENTS

2007/0213799 A1* 9/2007 Jolly .................... A61N 1/0541
607/137
2009/0062896 A1* 3/2009 Overstreet ........... A61K 9/0046
607/137

(Continued)

FOREIGN PATENT DOCUMENTS

KR        20210132130 A      11/2021
WO        2023192244 A1     10/2023

OTHER PUBLICATIONS

A. Qnouch, V. Solarczyk, J. Verin, G. Tourrel, P. Stahl, F. Danede, J.F. Willart, P.E. Lemesre, C. Vincent, J. Siepmann, F. Siepmann, Dexamethasone-Loaded Cochlear Implants: How to Provide a Desired "burst release", International Journal of Pharmaceutics: X, (Year: 2021).*

(Continued)

*Primary Examiner* — Matthew L Hamilton
(74) *Attorney, Agent, or Firm* — ALG Intellectual Property, LLC

(57) ABSTRACT

An exemplary system comprises a memory that stores instructions and a processor communicatively coupled to the memory and configured to execute the instructions to perform a process. The process may comprise accessing an individual three-dimensional ("3D") cochlea model of a cochlea of a recipient of a cochlear implant system that includes a stimulating lead inserted into the cochlea during a lead insertion procedure, generating, based on the individual 3D cochlea model and procedure data associated with one or more lead insertion procedures performed with respect to one or more other recipients, an individualized drug delivery profile for the recipient, and transmitting a command to the cochlear implant system to cause release of a drug from the stimulating lead in accordance with the individualized drug delivery profile.

20 Claims, 11 Drawing Sheets

(51) Int. Cl.
    *A61N 1/36*        (2006.01)
    *A61N 1/372*     (2006.01)
    *G16H 40/63*    (2018.01)

(56)        References Cited

U.S. PATENT DOCUMENTS

| 2013/0079749 | A1* | 3/2013 | Overstreet | ............. | A61K 45/06 |
| | | | | | 604/285 |
| 2021/0076990 | A1* | 3/2021 | Alimohammadi | ... | A61B 5/1473 |
| 2022/0367028 | A1 | 11/2022 | Avci et al. | | |
| 2024/0194335 | A1 | 6/2024 | Heasman et al. | | |
| 2025/0200930 | A1* | 6/2025 | Erpenbeck | ............. | G16H 30/20 |

OTHER PUBLICATIONS

Geerardyn et al. "Three-dimensional quantification of fibrosis and ossification after cochlear implantation via virtual re-sectioning: Potential implications for residual hearing". https://www.sciencedirect.com/science/article/pii/S0378595522002490. DOI:10.1016/j.heares.2022.108681Corpus ID: 254874075.
European Search Report received in EP Application No. 25180147.8 on Oct. 22, 2025.
Nemati Pedram et al., "Artificial neural networks for bilateral prediction of formulation parameters and drug release profiles from cochlear implant coatings fabricated as porous monolithic devices based on silicone rubber", Journal of Pharmacy and Pharmacology: JPP, vol. 66, No. 5, May 1, 2014, pp. 624-638.
Plontke S K et al., "Intracochlear drug delivery in combination with cochlear implants", HNO, Springer Medizin, Heidelberg, vol. 65, No. 1, Dec. 8, 2016, pp. 19-28.

\* cited by examiner

SYSTEMS AND METHODS FOR IMPLEMENTING AN INDIVIDUALIZED DRUG DELIVERY PROFILE FOR A RECIPIENT OF A COCHLEAR IMPLANT SYSTEM

BACKGROUND INFORMATION

Cochlear implant systems are used to provide, restore, and/or improve the sense of hearing to recipients with severe or profound hearing loss. Conventional cochlear implant systems include various components configured to be implanted within a recipient (e.g., an electronics package, an antenna, and an electrode lead) and various components configured to be located external to the recipient (e.g., a sound processor, a battery, and a microphone). Typically, at least some of the implanted components of a cochlear implant system are provided within an encapsulant formed of a biocompatible material such as medical grade silicone.

An electrode lead of a cochlear implant system typically includes an electrode array comprised of metal contacts (e.g., platinum, titanium, etc.) insulated by the medical grade silicone. Correct insertion and placement of the electrode lead within a cochlea is of great importance for effective electrical stimulation and effective use of the cochlear implant. For example, it is important for the electrode lead to stay within the scala tympani of the cochlea instead of translocating to the scala vestibuli, to be oriented correctly, and to minimize trauma to intracochlear structures so as to preserve any residual hearing that a cochlear implant recipient may have. Although progress has been made in reducing trauma during electrode lead insertion, the insertion of a foreign body such as an electrode lead within the cochlea is still likely to result in a certain degree of intracochlear trauma, induce fibrosis, and/or result in foreign body encapsulation.

Clinically feasible solutions to these challenges may involve repeated transtympanic administrations (e.g., of anti-inflammatory drugs) with a risk of off-target effects and significant burden for patients and/or the healthcare system. Further, intracochlear administrations post-implantation may cause damage to the implanted device and/or disrupt the local environment, leading to repeated risk of inflammation or infection. Alternative solutions have been proposed in which an electrode lead is impregnated with drugs that passively elute into the perilymph post insertion to treat the trauma. However, such approaches often result in the drugs being released at a time that is suboptimal and/or at a location within the cochlea where the drugs are not needed. Accordingly, there remains room to improve drug delivery to recipients of cochlear implants to facilitate preservation of intracochlear structures and residual hearing of the recipients.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for implementing an individualized drug delivery profile for a recipient of a cochlear implant system are described herein. An exemplary system comprises a memory that stores instructions and a processor communicatively coupled to the memory and configured to execute the instructions to perform a process. The process may comprise accessing an individual three-dimensional ("3D") cochlea model of a cochlea of a recipient of a cochlear implant system that includes a stimulating lead inserted into the cochlea during a lead insertion procedure, generating, based on the individual 3D cochlea model and procedure data associated with one or more lead insertion procedures performed with respect to one or more other recipients (i.e., one or more other recipients of cochlear implant systems), an individualized drug delivery profile for the recipient, and transmitting a command to the cochlear implant system to cause release of a drug from the stimulating lead in accordance with the individualized drug delivery profile.

The systems and methods described herein may provide various benefits to cochlear implant recipients, as well as others involved with managing cochlear implant systems. For example, the systems and methods described herein may beneficially facilitate generating and/or using drug delivery profiles that are individually tailored to a recipient of a cochlear implant system based on the size/shape their specific cochlea and/or the position of the stimulating lead within the cochlea. Such individual drug delivery profiles may result in localized distribution of drugs and/or compounds in a manner that facilitates preservation of intracochlear structures thereby increasing the chances of preserving residual (e.g., low frequency) hearing and/or increasing the chances of access to potential future therapies that may restore natural hearing. In addition, the systems and methods described herein may mitigate the effects of fibrosis and/or bone growth within the cochlea that may be caused by trauma, may limit speech performance over time, and/or may limit success of revision surgeries. Accordingly, systems and methods such as those described herein result in cochlear implant systems that are robust and can have a relatively long operational life.

Various embodiments will now be described in more detail with reference to the figures. The disclosed systems and methods may provide one or more of the benefits mentioned above and/or various additional and/or alternative benefits that will be made apparent herein.

Figure 1:
FIG. 1 illustrates an exemplary cochlear implant system.
Figure 1:
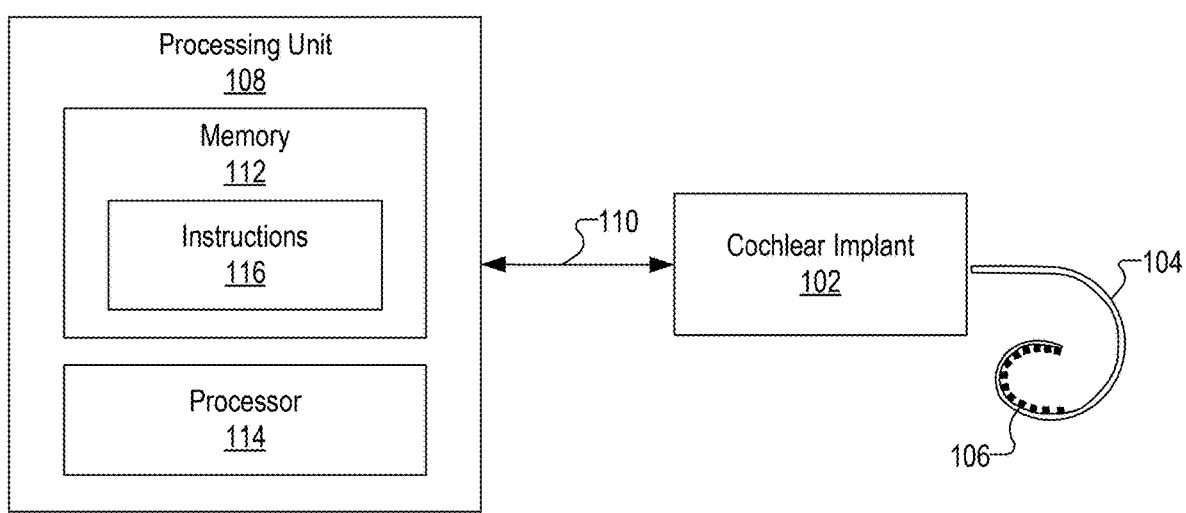

FIG. 1 illustrates an exemplary cochlear implant system 100 configured to be used by a recipient. As shown, cochlear implant system 100 includes a cochlear implant 102, a stimulating lead 104 physically coupled to cochlear implant 102 and having an array of stimulating portions 106, and a processing unit 108 configured to be communicatively coupled to cochlear implant 102 by way of a communication link 110.

The cochlear implant system 100 shown in FIG. 1 is unilateral (i.e., associated with only one ear of the recipient). Alternatively, a bilateral configuration of cochlear implant system 100 may include separate cochlear implants and stimulating leads for each ear of the recipient. In the bilateral configuration, processing unit 108 may be implemented by a single processing unit configured to interface with both cochlear implants or by two separate processing units each configured to interface with a different one of the cochlear implants.

Cochlear implant 102 may be implemented by any suitable type of implantable stimulator. For example, cochlear implant 102 may be implemented by an implantable cochlear stimulator. Additionally or alternatively, cochlear implant 102 may be implemented by a brainstem implant and/or any other type of device that may be implanted within the recipient and configured to apply optical and/or electrical stimulation to one or more stimulation sites located along an auditory pathway of the recipient.

In some examples, cochlear implant 102 may be configured to generate electrical stimulation representative of an audio signal processed by processing unit 108 in accordance with one or more stimulation parameters transmitted to cochlear implant 102 by processing unit 108. Cochlear implant 102 may be further configured to apply the electrical stimulation to one or more stimulation sites (e.g., one or more intracochlear locations) within the recipient by way of one or more stimulating portions 106 as electrodes on stimulating lead 104. In some examples, cochlear implant 102 may include a plurality of independent current sources each associated with a channel defined by one or more of the electrodes. In this manner, different stimulation current levels may be applied to multiple stimulation sites simultaneously by way of multiple electrodes.

In some examples, cochlear implant 102 may be configured to generate optical stimulation representative of an audio signal processed by processing unit 108 in accordance with one or more stimulation parameters transmitted to cochlear implant 102 by processing unit 108. Cochlear implant 102 may be further configured to apply the optical stimulation to one or more stimulation sites (e.g., one or more intracochlear locations that have been modified to be sensitive to optical stimulation) within the recipient by way of one or more optrodes on stimulating lead 104.

Cochlear implant 102 may additionally or alternatively be configured to generate, store, and/or transmit data. For example, in certain implementations, cochlear implant 102 may use one or more electrodes to record one or more signals (e.g., one or more voltages, impedances, evoked responses within the recipient, and/or other measurements) and transmit, by way of communication link 110, data representative of the one or more signals to processing unit 108. In some examples, this data is referred to as back telemetry data.

Stimulating lead 104 may be implemented in any suitable manner. For example, stimulating lead 104 may correspond to an electrode lead in certain implementations. In certain alternative implementations, stimulating lead 104 may correspond to an optrode lead. Alternatively, stimulating lead 104 may include a combination of both optrodes and electrodes. In certain examples, a distal portion of stimulating lead 104 may be pre-curved such that stimulating lead 104 conforms with the helical shape of the cochlea after being implanted. Stimulating lead 104 may alternatively be naturally straight or of any other suitable configuration.

In some examples, stimulating lead 104 may include a plurality of optrodes that are arranged on a flexible thin film substrate. In such examples, optrodes of stimulating lead 104 may include any suitable light emitting portion as may serve a particular implementation. For example, optrodes such as those described herein may include, point light sources, μLEDs, vertical cavity surface emitting lasers fabricated on flexible printed circuit boards, and/or polymer waveguides that are encapsulated by a flexible biocompatible material such as silicone, Parylene C, or polydimethylsiloxane ("PDMS"). Different exemplary configurations of stimulating lead 104 are described herein.

Stimulating portions 106 are located on at least a distal portion of stimulating lead 104. In this configuration, after the distal portion of stimulating lead 104 is inserted into the cochlea, optical and/or electrical stimulation may be applied by way of one or more of stimulating portions 106 to one or more intracochlear locations. Stimulating lead 104 may include any suitable number of stimulating portions 106 as may serve a particular implementation.

Processing unit 108 may be configured to interface with (e.g., control and/or receive data from) cochlear implant 102. For example, processing unit 108 may transmit commands (e.g., stimulation parameters and/or other types of operating parameters in the form of data words included in a forward telemetry sequence) to cochlear implant 102 by way of communication link 110. Processing unit 108 may additionally or alternatively provide operating power to cochlear implant 102 by transmitting one or more power signals to cochlear implant 102 by way of communication link 110. Processing unit 108 may additionally or alternatively receive data from cochlear implant 102 by way of communication link 110. Communication link 110 may be implemented by any suitable number of wired and/or wireless bidirectional and/or unidirectional links.

As shown, processing unit 108 includes a memory 112 and a processor 114 configured to be selectively and communicatively coupled to one another. In some examples, memory 112 and processor 114 may be distributed between multiple devices and/or multiple locations as may serve a particular implementation.

Memory 112 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 112 may maintain (e.g., store) executable data used by processor 114 to perform one or more of the operations described herein. For example, memory 112 may store instructions 116 that may be executed by processor 114 to perform any of the operations described herein. Instructions 116 may be implemented by any suitable application, program (e.g., sound processing program), software, code, and/or other executable data instance. Memory 112 may also maintain any data received, generated, managed, used, and/or transmitted by processor 114.

Processor 114 may be configured to perform (e.g., execute instructions 116 stored in memory 112 to perform) various operations with respect to cochlear implant 102.

To illustrate, processor 114 may be configured to control an operation of cochlear implant 102. For example, processor 114 may receive an audio signal (e.g., by way of a microphone communicatively coupled to processing unit 108, a wireless interface (e.g., a Bluetooth interface), and/or a wired interface (e.g., an auxiliary input port)). Processor 114 may process the audio signal in accordance with a sound processing program (e.g., a sound processing program stored in memory 112) to generate appropriate stimulation parameters. Processor 114 may then transmit the stimulation parameters to cochlear implant 102 to direct cochlear implant 102 to apply stimulation representative of the audio signal to the recipient by way of one or more of stimulating portions 106.

In some implementations, processor 114 may also be configured to apply acoustic stimulation to the recipient. For example, a receiver (also referred to as a loudspeaker) may be optionally coupled to processing unit 108. In this configuration, processor 114 may deliver acoustic stimulation to the recipient by way of the receiver. The acoustic stimulation may be representative of an audio signal (e.g., an amplified version of the audio signal), configured to elicit an evoked response within the recipient, and/or otherwise configured. In configurations in which processor 114 is configured to both deliver acoustic stimulation to the recipient and direct cochlear implant 102 to apply electrical stimulation and/or optical stimulation to the recipient, cochlear implant system 100 may be referred to as a bimodal hearing system and/or any other suitable term.

Processor 114 may be additionally or alternatively configured to receive and process data generated by cochlear implant 102. For example, processor 114 may receive data representative of a signal recorded by cochlear implant 102 using one or more electrodes and, based on the data, adjust one or more operating parameters of processing unit 108. Additionally or alternatively, processor 114 may use the data to perform one or more diagnostic operations with respect to cochlear implant 102 and/or the recipient.

Other operations may be performed by processor 114 as may serve a particular implementation. In the description provided herein, any references to operations performed by processing unit 108 and/or any implementation thereof may be understood to be performed by processor 114 based on instructions 116 stored in memory 112.

Figure 2:
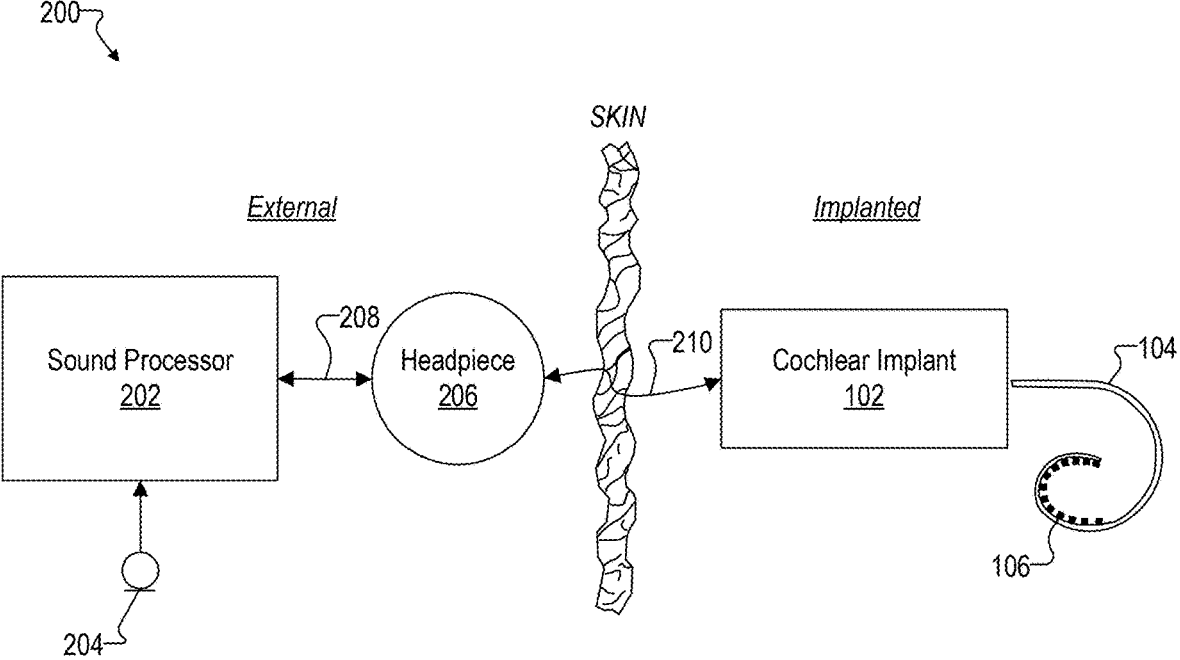
FIG. 2 shows an exemplary configuration of the cochlear implant system of FIG. 1.

Processing unit 108 may be implemented by one or more devices configured to interface with cochlear implant 102. To illustrate, FIG. 2 shows an exemplary configuration 200 of cochlear implant system 100 in which processing unit 108 is implemented by a sound processor 202 configured to be located external to the recipient. In configuration 200, sound processor 202 is communicatively coupled to a microphone 204 and to a headpiece 206 that are both configured to be located external to the recipient.

Sound processor 202 may be implemented by any suitable device that may be worn or carried by the recipient. For example, sound processor 202 may be implemented by a behind-the-ear ("BTE") unit configured to be worn behind and/or on top of an ear of the recipient. Additionally or alternatively, sound processor 202 may be implemented by an off-the-ear unit (also referred to as a body worn device) configured to be worn or carried by the recipient away from the ear. Additionally or alternatively, at least a portion of sound processor 202 is implemented by circuitry within headpiece 206.

Microphone 204 is configured to detect one or more audio signals (e.g., that include speech and/or any other type of sound) in an environment of the recipient. Microphone 204 may be implemented in any suitable manner. For example, microphone 204 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 202. Additionally or alternatively, microphone 204 may be implemented by one or more microphones in or on headpiece 206, one or more microphones in or on a housing of sound processor 202, one or more beam-forming microphones, and/or any other suitable microphone as may serve a particular implementation.

Headpiece 206 may be selectively and communicatively coupled to sound processor 202 by way of a communication link 208 (e.g., a cable or any other suitable wired or wireless communication link), which may be implemented in any suitable manner. Headpiece 206 may include an external antenna (e.g., a coil and/or one or more wireless communication components) configured to facilitate selective wireless coupling of sound processor 202 to cochlear implant 102. Headpiece 206 may additionally or alternatively be used to selectively and wirelessly couple any other external device to cochlear implant 102. To this end, headpiece 206 may be configured to be affixed to the recipient's head and positioned such that the external antenna housed within headpiece 206 is communicatively coupled to a corresponding implantable antenna (which may also be implemented by a coil and/or one or more wireless communication components) included within or otherwise connected to cochlear implant 102. In this manner, stimulation parameters and/or power signals may be wirelessly and transcutaneously transmitted between sound processor 202 and cochlear implant 102 by way of a wireless communication link 210.

In configuration 200, sound processor 202 may receive an audio signal detected by microphone 204 by receiving a signal (e.g., an electrical signal) representative of the audio signal from microphone 204. Sound processor 202 may additionally or alternatively receive the audio signal by way of any other suitable interface as described herein. Sound processor 202 may process the audio signal in any of the ways described herein and transmit, by way of headpiece 206, stimulation parameters to cochlear implant 102 to direct cochlear implant 102 to apply stimulation representative of the audio signal to the recipient.

In an alternative configuration, sound processor 202 may be implanted within the recipient instead of being located external to the recipient. In this alternative configuration, which may be referred to as a fully implantable configuration of cochlear implant system 100, sound processor 202 and cochlear implant 102 may be combined into a single device or implemented as separate devices configured to communicate one with another by way of a wired and/or wireless communication link. In a fully implantable implementation of cochlear implant system 100, headpiece 206 may not be included and microphone 204 may be implemented by one or more microphones implanted within the recipient, located within an ear canal of the recipient, and/or external to the recipient.

Figure 3:
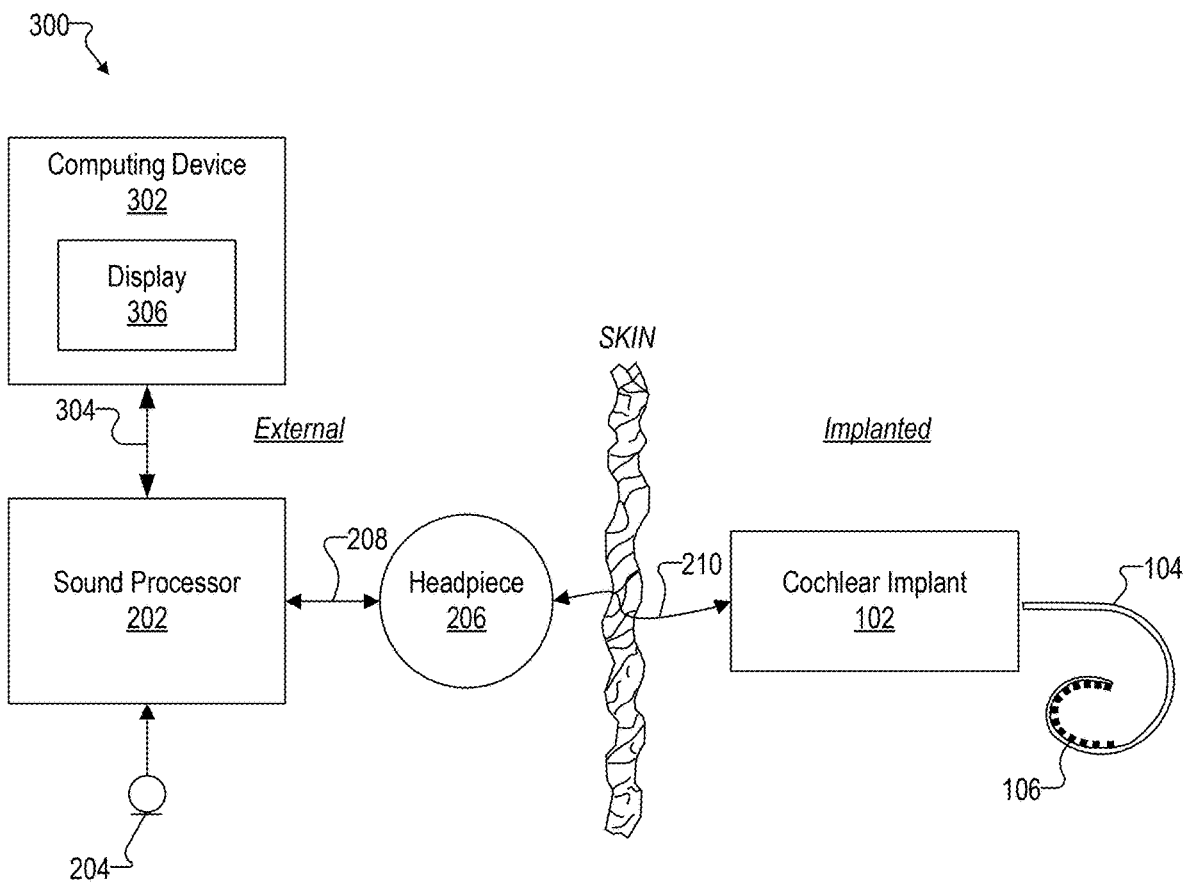
FIG. 3 shows another exemplary configuration of the cochlear implant system of FIG. 1.

FIG. 3 shows an exemplary configuration 300 of cochlear implant system 100 in which processing unit 108 is implemented by a combination of sound processor 202 and a computing device 302 configured to communicatively couple to sound processor 202 by way of a communication link 304, which may be implemented by any suitable wired or wireless communication link.

Computing device 302 may be implemented by any suitable combination of hardware and software. To illustrate, computing device 302 may be implemented by a mobile device (e.g., a mobile phone, a laptop, a tablet computer, etc.), a desktop computer, and/or any other suitable computing device as may serve a particular implementation. As an example, computing device 302 may be implemented by a mobile device configured to execute an application (e.g., a "mobile app") that may be used by a user (e.g., the recipient, a clinician, and/or any other user) to control one or more settings of sound processor 202 and/or cochlear implant 102 and/or perform one or more operations (e.g., diagnostic operations) with respect to data generated by sound processor 202 and/or cochlear implant 102.

In some examples, computing device 302 may be configured to control an operation of cochlear implant 102 by transmitting one or more commands to cochlear implant 102 by way of sound processor 202. Likewise, computing device 302 may be configured to receive data generated by cochlear implant 102 by way of sound processor 202. Alternatively, computing device 302 may interface with (e.g., control and/or receive data from) cochlear implant 102 directly by way of a wireless communication link between computing device 302 and cochlear implant 102. In some implementations in which computing device 302 interfaces directly with cochlear implant 102, sound processor 202 may or may not be included in cochlear implant system 100.

Computing device 302 is shown as having an integrated display 306. Display 306 may be implemented by a display screen, for example, and may be configured to display content generated by computing device 302. Additionally or alternatively, computing device 302 may be communicatively coupled to an external display device (not shown) configured to display the content generated by computing device 302.

In some examples, computing device 302 represents a fitting device configured to be selectively used (e.g., by a clinician) to fit sound processor 202 and/or cochlear implant 102 to the recipient. In these examples, computing device 302 may be configured to execute a fitting program configured to set one or more operating parameters of sound processor 202 and/or cochlear implant 102 to values that are optimized for the recipient. As such, in these examples, computing device 302 may not be considered to be part of cochlear implant system 100. Instead, computing device 302 may be considered to be separate from cochlear implant system 100 such that computing device 302 may be selectively coupled to cochlear implant system 100 when it is desired to fit sound processor 202 and/or cochlear implant 102 to the recipient.

Figure 4:
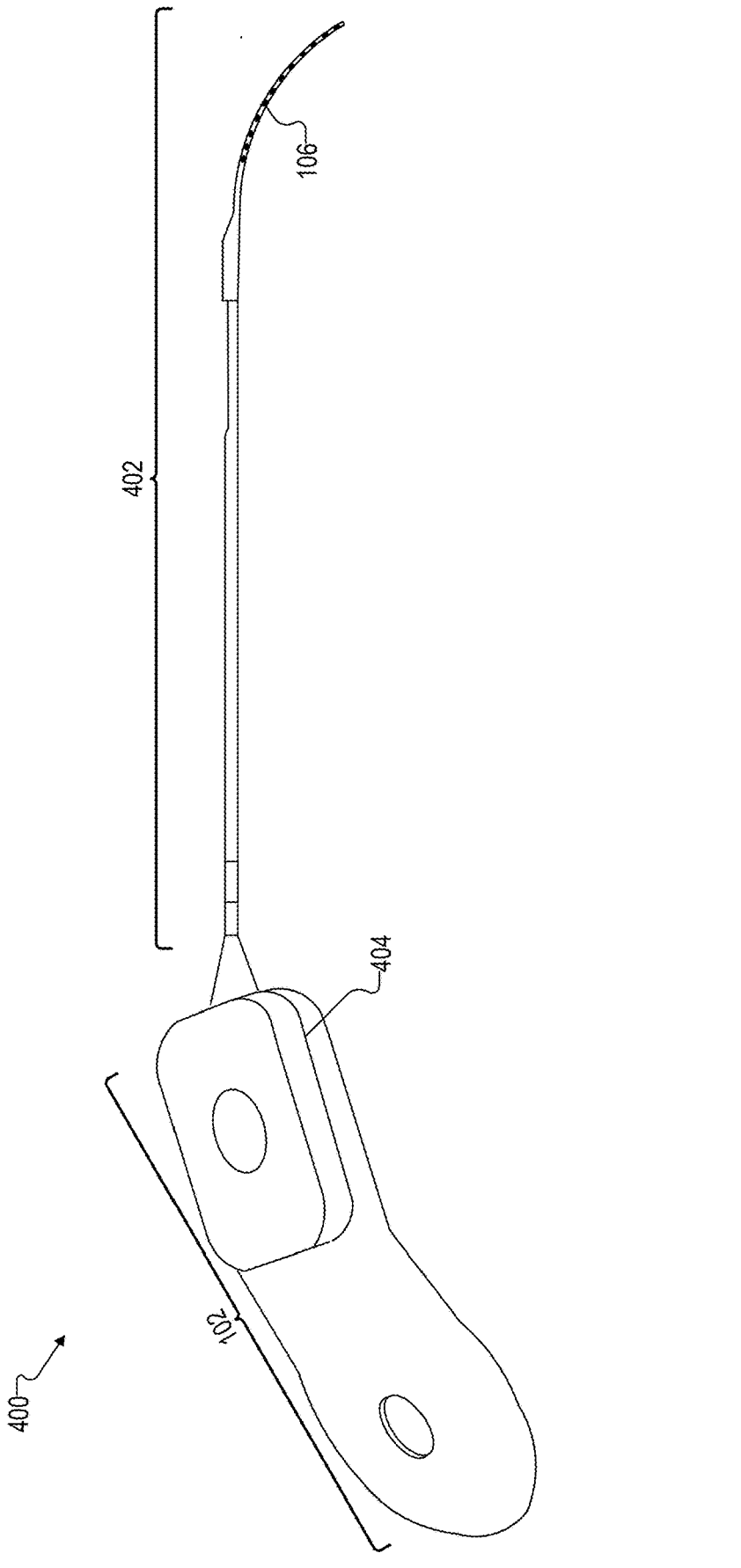
FIG. 4 shows an exemplary cochlear implant assembly according to principles described herein.

FIG. 4 illustrates an exemplary cochlear implant assembly 400 that is adapted for insertion into a recipient. As shown in FIG. 4, cochlear implant assembly 400 includes a stimulating lead 402 that is communicatively coupled to an implantable cochlear implant stimulator ("ICS") 404 that is included as part of cochlear implant 102. ICS 404 may be configured to deliver electrical stimulation and/or optical stimulation to a recipient by way of one or more stimulating portions (e.g., electrodes and/or optrodes) included in a plurality of stimulating portions 106 of stimulating lead 402. In the example shown in FIG. 4, plurality of stimulating portions 106 are arranged in an array along the length of stimulating lead 402.

An elastomeric encapsulant is provided as part of a cochlear implant to protect certain components of a cochlear implant system while such components are implanted within a recipient. For example, an elastomeric encapsulant may encapsulate ICS 404, stimulating lead 402, and/or any other suitable component.

Elastomeric encapsulants may be formed of any suitable material as may serve a particular implementation. For example, elastomeric encapsulants may be formed of silicone and/or any other suitable biocompatible material. In certain examples, an outermost layer of an elastomeric encapsulant may include an anti-fibrotic coating that fully encapsulates ICS 404, stimulating lead 402, and/or any other suitable component. Such an anti-fibrotic coating may be configured to prevent or mitigate fibrotic tissue growth that would otherwise reduce stimulation efficiency. Any suitable anti-fibrotic coating may be used as may serve a particular implementation.

Elastomeric encapsulants such as those described herein may be formed in any suitable manner as may serve a particular implementation. In certain examples, an elastomeric encapsulant may be overmolded around certain components (e.g., cochlear implant 102, stimulating lead 104, 402, etc.) of cochlear implant system 100. Alternatively, an elastomeric encapsulant may be formed through casting, spraying, dipping, or any other suitable manufacturing method.

Elastomeric encapsulants such as those described herein may further include one or more portions that are impregnated with one or more compounds and/or drugs. For example, an elastomeric encapsulant may include one or more portions impregnated with dexamethasone, which is a steroid that inhibits the process of inflammation within the cochlea and may limit the buildup of intracochlear fibrosis. In examples where stimulating lead 402 corresponds to an optrode lead, the compound may additionally or alternatively include a compound or drug that facilitates light sensitivity of neurons of the cochlea. Elastomeric encapsulants may include any suitable number of portions impregnated with the compound as may serve a particular implementation. For example, in certain implementations, a single portion may be impregnated with the compound. Alternatively, an elastomeric encapsulant may include a plurality of separate portions that are impregnated with the compound. Exemplary configurations of such portions that may be impregnated with the compound/drug are described herein.

As used herein, a "drug" may correspond to any suitable medicine, compound, pharmaceutical, etc. that may be used to beneficially treat a recipient of a cochlear implant system. A drug impregnated within a stimulating lead such as stimulating lead 104 may correspond to any suitable type of drug and/or combination of drugs as may serve a particular implementation. For example, the drug may include any suitable drugs that may suppress an immunogenic response (e.g., immunosuppressants such as dexamethasone and its variants), suppress inflammation, and/or promote neural survival (e.g., neurotrophic factors such as BDNF or NT-3) and that may be impregnated within an elastomeric encapsulant of stimulating lead 402. In certain examples, the compound may incorporate liposomes that contain lipid nanoparticles which are then embedded within the elastomeric encapsulant.

Certain examples of stimulating leads may include gels or PDMS that are loaded with a certain amount of a drug such as dexamethasone. In such examples, as soon as the stimulating lead is inserted into the fluid filled cochlea, a passive diffusion process may take place and the drug may be released into the cochlea. Although this technology is advantageous as compared to intravenous application of steroids, several limitations remain. For example, there is typically a delay between completion of a lead insertion procedure and the onset of inflammation. As such, a passive diffusion of the drug may result in the bulk of the drug being released prior to when the drug is needed. In addition, such technology does not take into consideration where trauma occurs within the cochlea and/or where release of the drug may be most useful. In contrast, systems and methods such as those described herein are capable of generating an individualized drug delivery profile for a recipient that may be used to provide a drug at an optimal localized position within the cochlea and at a time where the drug will be most effective in treating the trauma and/or mitigated the associated effects. As will be described further herein, the generating of an individualized drug delivery profile may be accomplished by leveraging information associated with the size/shape of the cochlea for a given recipient, the location of the stimulating lead within the cochlea of that recipient, and/or procedure data associated with lead insertion procedures performed with respect to one or more other recipients.

Figure 5:
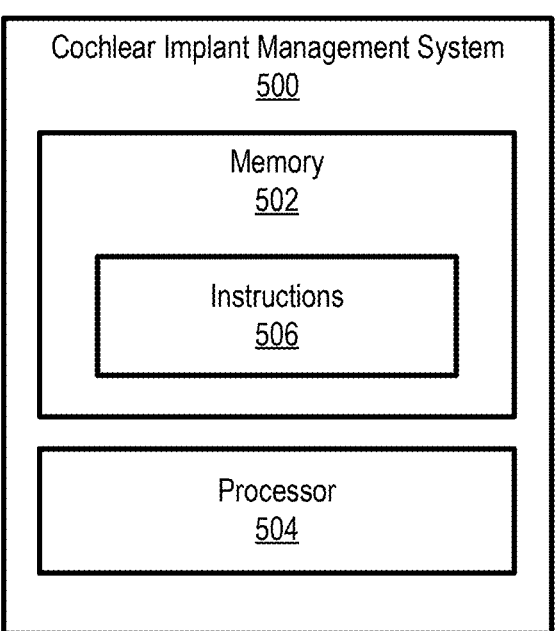
FIG. 5 shows an exemplary cochlear implant management system that may be implemented according to principles described herein.

To that end, FIG. 5 shows an exemplary cochlear implant management system 500 ("system 500") that may be implemented according to principles described herein to facilitate implementing an individualized drug delivery profile for a recipient. As shown, system 500 may include, without limitation, a memory 502 and a processor 504 selectively and communicatively coupled to one another. Memory 502 and processor 504 may each include or be implemented by hardware and/or software components (e.g., processors, memories, communication interfaces, instructions stored in memory for execution by the processors, etc.). In some examples, memory 502 and/or processor 504 may be implemented by any suitable computing device. In other examples, memory 502 and/or processor 504 may be distributed between multiple devices and/or multiple locations as may serve a particular implementation. Illustrative implementations of system 500 are described herein.

Memory 502 may maintain (e.g., store) executable data used by processor 504 to perform any of the operations described herein. For example, memory 502 may store instructions 506 that may be executed by processor 504 to perform any of the operations described herein. Instructions 506 may be implemented by any suitable application, software, code, and/or other executable data instance.

Memory 502 may also maintain any data received, generated, managed, used, and/or transmitted by processor 504. Memory 502 may store any other suitable data as may serve a particular implementation. For example, memory 502 may store data associated with 3D cochlea models, procedure data (e.g., statistical data associated with previous lead insertion procedures performed with respect to other recipients), pre-operative scan images, post-operative scan images, stimulating lead type information, cochlear implant information (e.g., electrode lead dimensions information), graphical user interface content, and/or any other suitable data.

Processor 504 may be configured to perform (e.g., execute instructions 506 stored in memory 502 to perform) various processing operations associated with implementing an individual drug delivery profile for a recipient of a cochlear implant system. For example, processor 504 may perform one or more operations described herein to generate, based on the individual 3D cochlea model and procedure data, an individualized drug delivery profile for the recipient. These and other operations that may be performed by processor 504 are described herein.

System 500 may be implemented in any suitable manner. For example, system 500 may be implemented by any suitable computing device (e.g., a desktop computer, a laptop computer, a cloud computing device, etc.) that may be configured to process scan images, procedure data, individual 3D cochlea models, and/or any other suitable information to generate an individualized drug delivery profile that is specific to a particular recipient of a cochlear implant system. In certain examples, system 500 may include a scanning device, may be communicatively coupled to a scanning device, or may otherwise receive, in any suitable manner, pre-operative and/or post-operative scan images of the cochlea captured by a scanning device.

In certain examples, the methods described herein may be performed automatically by system 500. As used herein, the expression "automatically" means that an operation (e.g., an operation of simulating a lead insertion procedure) or series of operations are performed without requiring further input from a user. For example, system 500 may automatically perform any of the operations described herein to generate an individualized drug delivery profile without requiring further input from a user.

Figure 6:
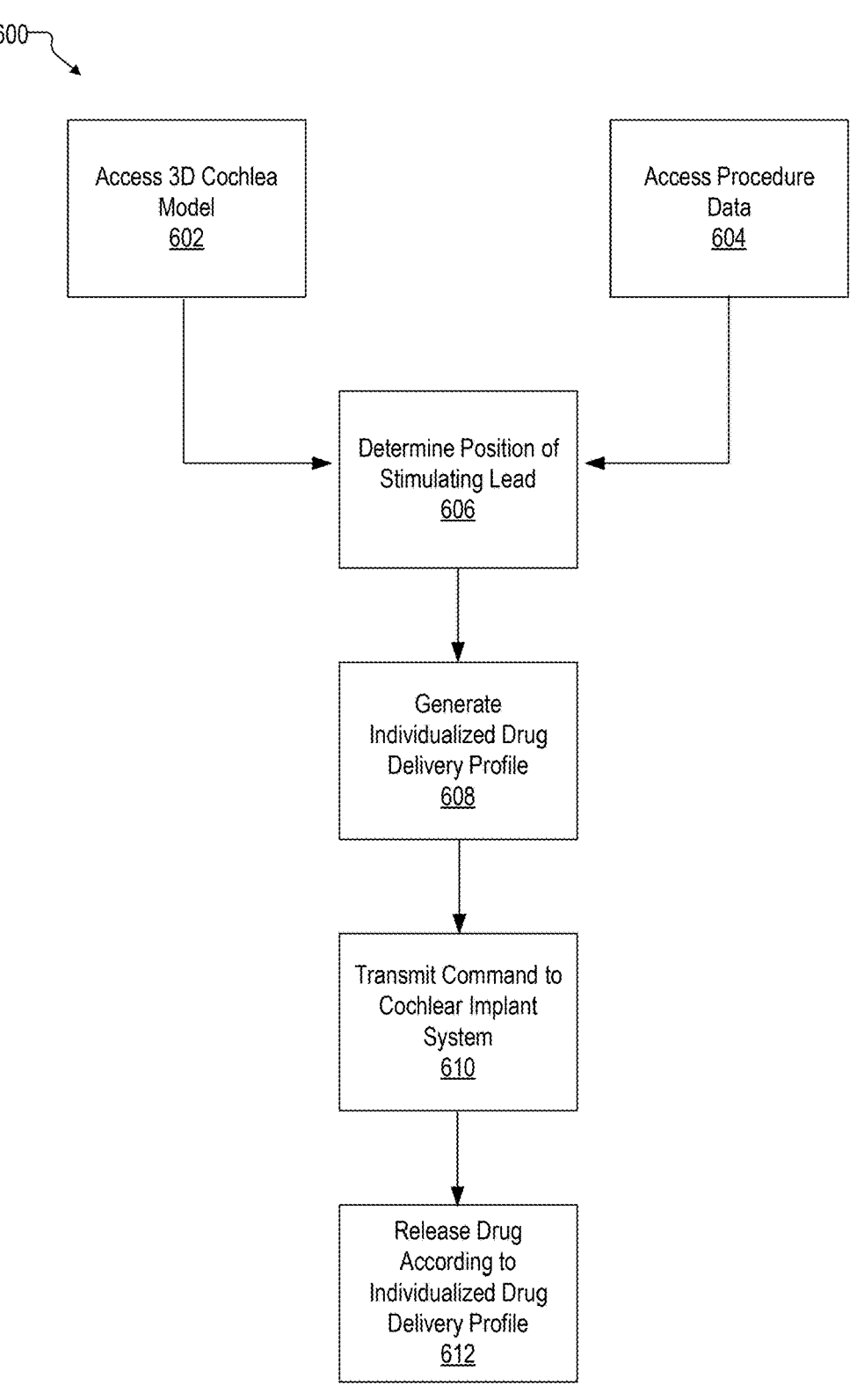
FIG. 6 is an exemplary flow diagram with various operations that may be performed by the cochlear implant management system shown in FIG. 5 according to principles described herein.

FIG. 6 illustrates an exemplary flow diagram 600 that depicts various operations that may be performed by system 500 to facilitate implementing an individual drug delivery profile for a recipient. As shown in FIG. 6, system 500 may access an individual 3D cochlea model of a recipient of a cochlear implant system at operation 602. System 500 may access the individual 3D cochlea model in any suitable manner. In certain examples, system 500 may obtain an already generated individual 3D cochlea model from any suitable source such as a third party. Alternatively, system 500 may be configured to generate an individual 3D cochlea model for a recipient in any suitable manner. For example, an individual 3D cochlea model may be generated based on an active shape model ("ASM"). An ASM is a statistical shape model ("SSM") of a shape (e.g., a cochlea) that deforms to fit an example that shape. An SSM is a geometric model that describes a collection of semantically similar shapes in a compact way and may be composed of an average shape as well as the main modes of shape variations. An individual 3D model may represent an ASM that has been deformed to fit one or more determined or estimated surfaces of the cochlea such as a surface of the cochlea wall and/or a surface of the basilar membrane, resulting in an estimation of the anatomical structure of the cochlea for a specific recipient.

At operation 604, system 500 may access procedure data associated with one or more lead insertion procedures performed with respect to one or more other recipients. The procedure data may include any suitable information that may be associated with past lead insertion procedures performed with respect to the recipient (e.g., with respect to a different ear) and/or other recipients. For example, procedure data may include, but is not limited to, data indicative of one or more locations where trauma typically occurs during and/or after a lead insertion procedure, the type of stimulating leads inserted, the age of the recipients, 3D cochlea models of the recipients, statistical insertion depth and/or position information, and/or any other suitable information. To illustrate an example, for a lateral wall type stimulating lead, the procedure data may indicate that the lateral cochlea region around 90-150° from the round window is typically negatively impacted by forces during a lead insertion procedure, resulting in damage to the endosteum and/or spiral ligament.

System 500 may access the procedure data from any suitable source. For example, system 500 may access the procedure data from a database that stores any suitable statistical information regarding lead insertion procedures performed with respect to a plurality of recipients.

At operation 606, system 500 may determine a position of a stimulating lead within the cochlea. This may be accomplished in any suitable manner. For example, in certain implementations, system 500 may perform, based on an individual 3D cochlea model, a simulation to determine an estimated position of a stimulating lead within the cochlea. System 500 may perform the simulation in any suitable manner. For example, system 500 use pre-operative scan images (e.g., computed tomography ("CT") images and/or magnetic resonance imaging ("MRI") images) to simulate the insertion and placement of a stimulating lead within the cochlea. The simulation may be based on either a static insertion model or a dynamic insertion model. In certain examples, system 500 may leverage 3D cochlea models of other recipients that have a cochlea of a similar shape and/or size of the recipient in performing the simulation. System 500 may further access procedure data associated with the lead insertion procedures performed with respect to those other recipients to determine an estimated position the stimulating lead within the cochlea.

Different types of stimulating leads may result in different insertion trajectories and/or placement within the cochlea. Accordingly, in certain examples, the simulation may be further based on a type of stimulating lead (e.g., pre-curved, lateral, hybrid, etc.) that will be or has been inserted during the lead insertion procedure. For example, system 500 may perform a first simulation based on a first type of stimulation lead, a second simulation based on a second type of stimulation lead, and a third simulation based on a third type of stimulation lead.

In certain alternative implementations, system 500 may determine, based on an individual 3D cochlea model and post-operative scan images of the recipient, a position of the stimulating lead within the cochlea. The post-operative scan images may include any suitable type of images as may serve a particular implementation. For example, the post-operative scan images may include CT images, MRI images, and/or any other suitable type of images. The post-operative scan images may include any suitable number of post-operative scan images as may serve a particular implementation.

System 500 may determine the position of the stimulating lead based on the post-operative scan images in any suitable manner. For example, system 500 may register the post-operative scan images with the individual 3D cochlea model. This may be accomplished by optimizing alignment of the post-operative scan images with the individual 3D cochlea model based on an intensity of all pixels (e.g., voxels) and a metric (e.g., mutual information between the post-operative scan images and the individual 3D cochlea model). In so doing, regions of high intensity (e.g., bright spots or blobs) in the post-operative scan images that may be indicative of stimulating portion (e.g., electrode contact)

positions may be aligned with corresponding positions in pre-operative scan images and the individual 3D cochlea model. System 500 may determine candidate positions of the stimulating portions based on the regions of high intensity and determine an estimated path of the stimulating lead based on multiple regions of high intensity. System 500 may determine the position of the stimulating lead based on the determined estimated path of the stimulating lead.

At operation 608, system 500 may generate an individualized drug delivery profile for the recipient based on the individual 3D model accessed at operation 602, the procedure data accessed at operation 604, and the position of the stimulating lead determined at operation 606. As used herein an "individualized drug delivery profile" may define any suitable parameters associated with the release of one or more drugs or compounds from a stimulating lead in a controlled manner that is specific to the recipient. For example, an individualized drug delivery profile may specify the timing for the release of the drug from the stimulating lead. For example, the individualized drug delivery profile may specify that the drug will be released a predefined amount of time after completion of the lead insertion procedure.

In certain examples, system 500 may take into consideration the volume of the cochlea or the scala tympani in generating the individualized drug delivery profile for a recipient. Based on the volume of the cochlea or the scala tympani, the individualized drug delivery profile may either specify a lower dose of the drug (e.g., to minimize risk of toxic overload) or specify a larger dose of the drug (e.g., to compensate for a loss of drug intake).

In addition, an individualized drug delivery profile may specify which portion of a stimulating lead will release a drug and in what amount, frequency, and/or duration. For example, an individualized drug delivery profile may indicate that a drug such as dexamethasone is to be released in relatively higher volumes from one or more portions of a stimulating lead as compared to other portions of the stimulating lead. To illustrate, a first portion of the stimulating lead may be located at a position within the cochlea that is subject to trauma, fibrosis, and/or inflammation that occur at least one of during a lead insertion procedure or after the lead insertion procedure. In such examples, the individualized drug delivery profile may indicate that the drug is to be released from the first portion of the stimulating lead that includes only a subset of stimulating portions included in a plurality of stimulating portions of the stimulating lead.

In certain examples, system 500 may adjust or modify an individualized drug delivery profile based on information derived from an individual 3D cochlea model. For example, system 500 analyze the individual 3D cochlea model in any suitable manner to determine whether there has been any contact or potential injury to the basilar membrane, the organ of corti, and/or the osseous spiral lamina. Even though such trauma may result in a certain amount of permanent damage, a localized relatively high dose of a drug according to the individualized drug delivery profile in those regions may reduce fibrotic tissue growth in the affected portions of the cochlea.

The individualized drug delivery profile may specify any suitable number of portions along the stimulating lead where the drug is to be controllably released. For example, the individualized drug delivery profile may specify that the drug is also to be released from a second portion of the stimulating lead that includes only an additional subset of stimulating portions included in the plurality of stimulating portions. In certain examples, the first portion of the stimulating lead and the second portion of the stimulating lead may be separated along the length of the stimulating lead by a third portion of the stimulating lead from which the drug is either not released or is released in a relatively lower volume. To illustrate an example, the first portion of the stimulating lead may include one or more stimulating portions on a distal end of the stimulating lead. The second portion of the stimulating lead may include one or more stimulating portions in a middle portion of the stimulating lead. The third portion of the stimulating lead may include one or more stimulating portions provided between the distal end of the stimulating lead and the middle portion of the stimulating lead.

Figure 7:
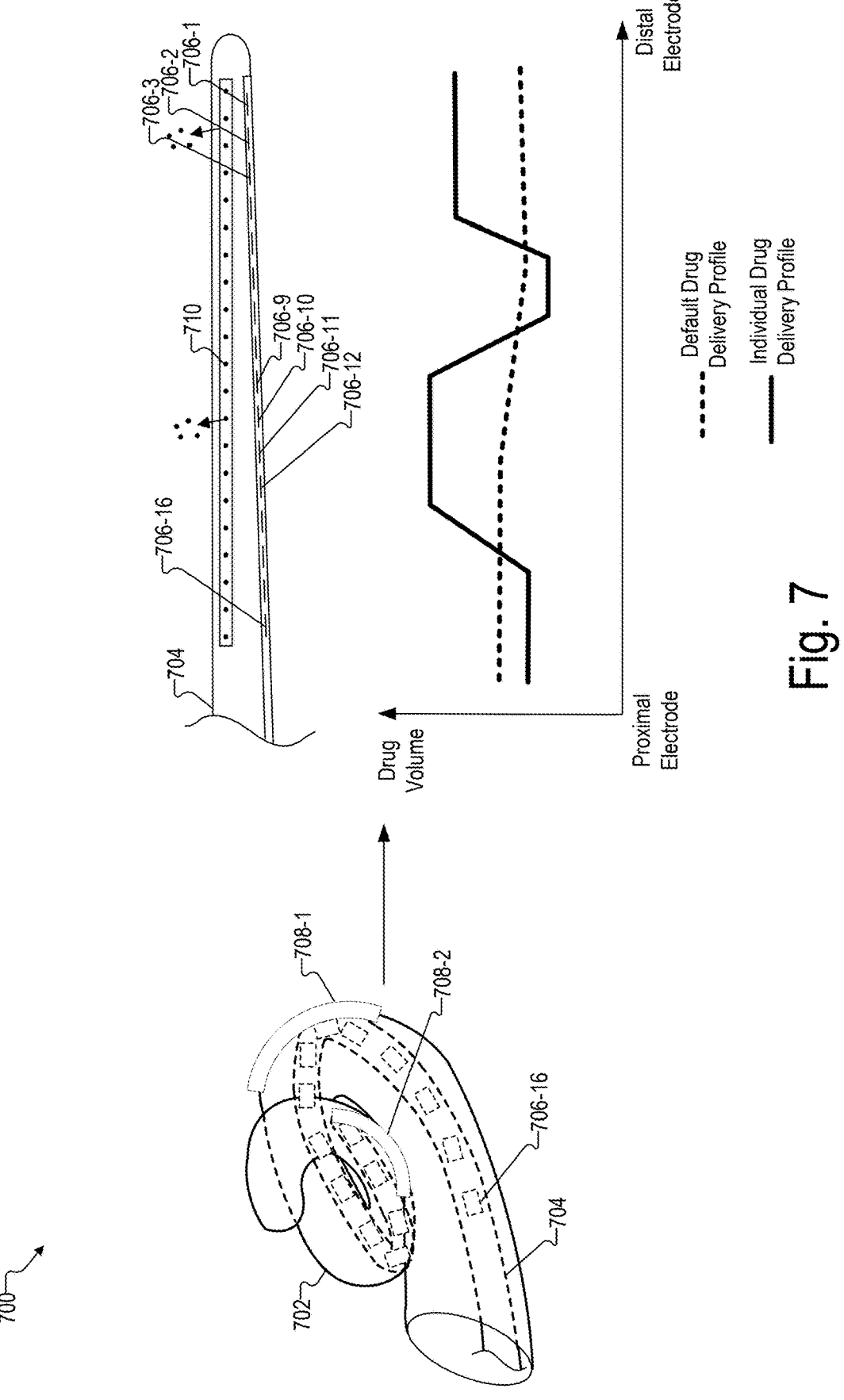
FIG. 7 shows a diagram depicting an exemplary 3D cochlea model and a configuration of an exemplary drug delivery profile that may be implemented according to principles described herein.

FIG. 7 shows an exemplary diagram 700 depicting an exemplary individualized drug delivery profile that may be generated based on an individual 3D cochlea model. As shown in FIG. 7, an individual 3D cochlea model 702 is depicted for illustrative purposes with a stimulating lead 704 disposed therein. Stimulating lead 704 includes a plurality of stimulating portions 706 (e.g., stimulating portions 706-1 through 706-16) arranged along a length of stimulating lead 704. Based on procedure data, system 500 may determine that there are one or more regions where trauma is likely to occur as a result of stimulating lead 704 being positioned within the cochlea. In the example shown in FIG. 7, regions 708-1 and 708-2 have been identified as regions that may have the highest risk of inflammation, fibrosis, and/or trauma. However, it is understood that any suitable number of regions may be identified as may serve a particular implementation. Based on the determined or estimated position of stimulating lead 704 within the cochlea, system 500 may determine that stimulating portions 706-1 through 706-3 are positioned adjacent to region 708-1 and that stimulating portions 706-9 through 706-12 are positioned adjacent to region 708-2. Accordingly, system 500 may generate an individualized drug delivery profile that will result in stimulating lead 704 controllably releasing a relatively larger volume of a drug 710 to regions 708-1 and 708-2 as compared to other regions, as shown in the graph in FIG. 7. As a result, the individualized drug delivery profile may beneficially result in a targeted and localized release of the drug to the regions where the drug may be needed the most.

Returning to FIG. 6, at operation 610, system 500 may transmit a command to the cochlear implant system that instructs the cochlear implant system to release the drug according to the individualized drug delivery profile. The command may be transmitted in any suitable manner using any suitable communication technology such as those described herein.

System 500 may transmit the command at any suitable time. For example, the command may be transmitted a predefined amount of time subsequent to completion of the lead insertion procedure based on the individualized drug delivery profile. To illustrate an example, the peak amount of inflammation resulting from a lead insertion procedure may occur 2-3 days post implantation. Accordingly, system 500 may wait to provide the command until 2-3 days after the lead insertion procedure to ensure that the drug is adequately provided to address the relatively high amount of inflammation. In certain examples, the command may be provided continually or periodically during a time period after the predefined amount of time. For example, the command may be provided periodically after two days post-insertion and for two weeks to controllably release the drug during that time period.

In addition, the command may include any suitable information to cause a stimulating lead to localize release of a drug in accordance with an individualized drug delivery profile. For example, the command to the cochlear implant system may cause the drug to be released from a first portion of the stimulating lead that includes only a subset of stimulating portions included in the plurality of stimulating portions. The command may further cause the drug to be released from a second portion of the stimulating lead that includes only an additional subset of stimulating portions included in the plurality of stimulating portions. Portions of the lead that include other stimulating portions but that do not include the subset or the additional subset of the stimulating portions may either not release the drug or may release a relatively lower volume of the drug.

At operation 612, the cochlear implant system may release the drug according to the individualized drug delivery profile based on the command. A drug may be controllably released from a stimulating lead such as stimulating lead 402 in any suitable manner using any suitable release mechanism. For example, the command may direct the cochlear implant system to provide electrical current by way of one or more electrode contacts included in the plurality of electrode contacts to cause release of the drug from the electrode lead. In such examples, a stimulating lead may include miniature valves or membranes provided along a length of the stimulating lead that may be controllably opened to release a drug in response to a small amount of voltage/current. Such miniature valves or membranes may facilitate release of a local high dose of the drug at one or more identified regions within the cochlea. In certain examples, the electrical current may be provided by an electrode that also is configured to provide electrical stimulation representative of an audio signal to the recipient. In certain alternative examples, the electrical current may be provided by an electrode that is dedicated to facilitate release of the drug.

In certain examples, a stimulating lead may additionally or alternatively include one or more drug impregnated portions (e.g., a polymer or gel type strip) arranged along a length of the stimulating lead. The drug impregnated portions may include a drug that is sensitive to small and local electric fields. In certain examples, such drug impregnated portions may include nanoparticles (e.g., lipid nanoparticles) that contain the drug and are configured to rupture and release the drug in response to the local electric field.

In certain alternative examples, temperature and/or any suitable chemical reaction may be used to controllably release the drug from the stimulating lead according to the individualized drug delivery profile.

In certain alternative examples, system 500 may use light emitted from optrodes of a stimulating lead to controllably trigger the release of the drug in accordance with an individualized drug delivery profile. In such examples, the command may include directing the cochlear implant system to emit light by way of one or more optrodes included in a plurality of optrodes to cause release of the drug from the optrode lead. In certain examples, the optrodes may be dedicated only to be used to controllably release the drug and a plurality of electrodes may be used to provide electrical stimulation to represent and audio signal to the recipient.

In certain alternative examples where the neurons of the cochlea are configured to be optically stimulated (e.g., by way adeno-associated virus ("AAV") technology), the optrodes may be used both to controllably release the drug and to stimulate the neurons in the cochlea. In such examples, system 500 may use a different wavelength of light to optically stimulate neurons of the cochlea than is used to trigger release of the drug. For example, system 500 may direct cochlear implant 102 to emit first light having a first wavelength by way of one or more optrodes of an optrode lead inserted at least partially within a cochlea of a recipient. The light having a first wavelength may be configured to optically stimulate neurons of the cochlea. System 500 may further direct cochlear implant 102 to emit light having a second wavelength by way of the one or more optrodes, the second wavelength being different than the first wavelength. The second wavelength is configured to trigger release of a compound that is impregnated within the optrode lead and that facilitates light sensitivity of the neurons.

Figure 8:
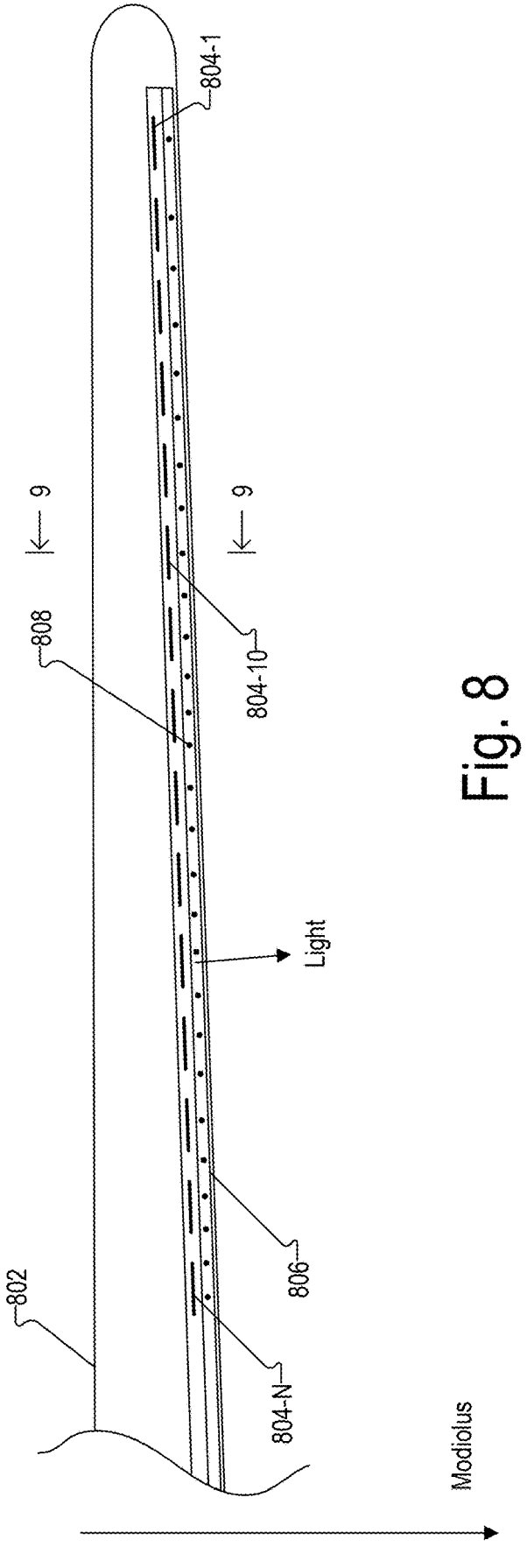
FIG. 8 shows an exemplary stimulating lead that may be implemented according to principles described herein.

To illustrate an example, FIG. 8 shows an exemplary side view of an optrode lead 800 that includes an elastomeric encapsulant 802 and a plurality of optrodes 804 (e.g., optrodes 804-1 through 804-N). As shown in FIG. 8, optrode lead 800 further includes a drug-impregnated section 806 that includes a drug 808, which may correspond to any suitable type of drug or combination of drugs or compounds such as described herein. In the example shown in FIG. 8, drug 808 is configured to be controllably released in any suitable manner such as described herein from optrode lead 800 in response to light emitted from one or more of optrodes 804.

Figure 9:
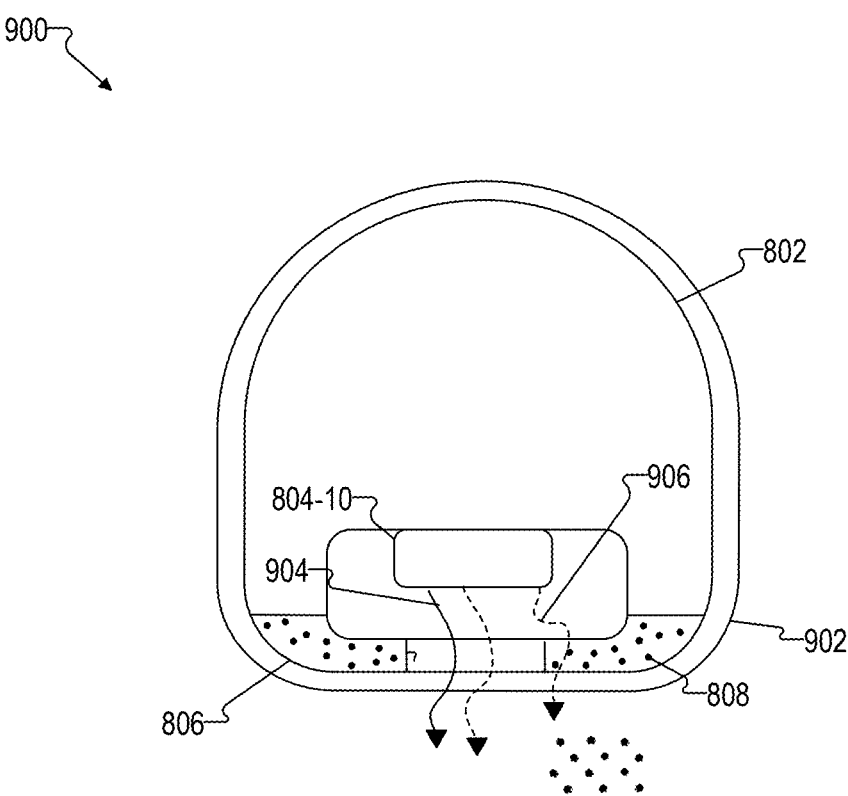
FIG. 9 is an exemplary cross-section of the stimulating lead shown in FIG. 8 taken along lines 9-9 in FIG. 8 according to principles described herein.

To illustrate, FIG. 9 shows a cross-sectional view 900 of optrode lead 800 taken along line 9-9 in FIG. 8. In the example shown in FIG. 9, optrode lead 800 includes an anti-fibrotic coating 902 that fully encapsulates optrode lead 800. As shown in FIG. 9, optrode 804-10 may emit light 904 having a first wavelength that is configured to provide optical stimulation to neurons in the cochlea and light 906 having a second wavelength that is configured to controllably trigger release of drug 808 from compound-impregnated section 806. In the example shown in FIG. 9, light 904 may correspond to light in a visible range such as a red light range and light 906 may correspond to light in a non-visible range such as NIR light.

In certain examples, system 500 may provide one or more graphical user interface views for display to a user (e.g., a physician) to facilitate fitting a cochlear implant system to a recipient and/or evaluating individualized drug delivery profiles. In such examples, the user may be able to review an individualized drug delivery profile and adjust one or more parameters of the individualized drug delivery profile through user input. For example, system 500 may provide user selectable options by way of a graphical user interface that facilitate the user selectively adjusting when the command is provided, at what frequency the command is provided, at what duration the command is provided, the stimulation portions used to trigger release of the drug, and/or any other suitable parameter.

Although the preceding disclosure describes stimulating leads configured for use with a cochlear implant system (e.g., cochlear implant system 100), it is understood that concepts such as those described herein may be applied to any other suitable type of implantable stimulator or externally used stimulator that may be implemented in any other suitable context. For example, concepts such as those described herein may be applied to stimulating leads used in neuroprosthetic systems, neurostimulation systems, optical nerve stimulation systems, cardiac stimulation systems, etc.

Figure 10:
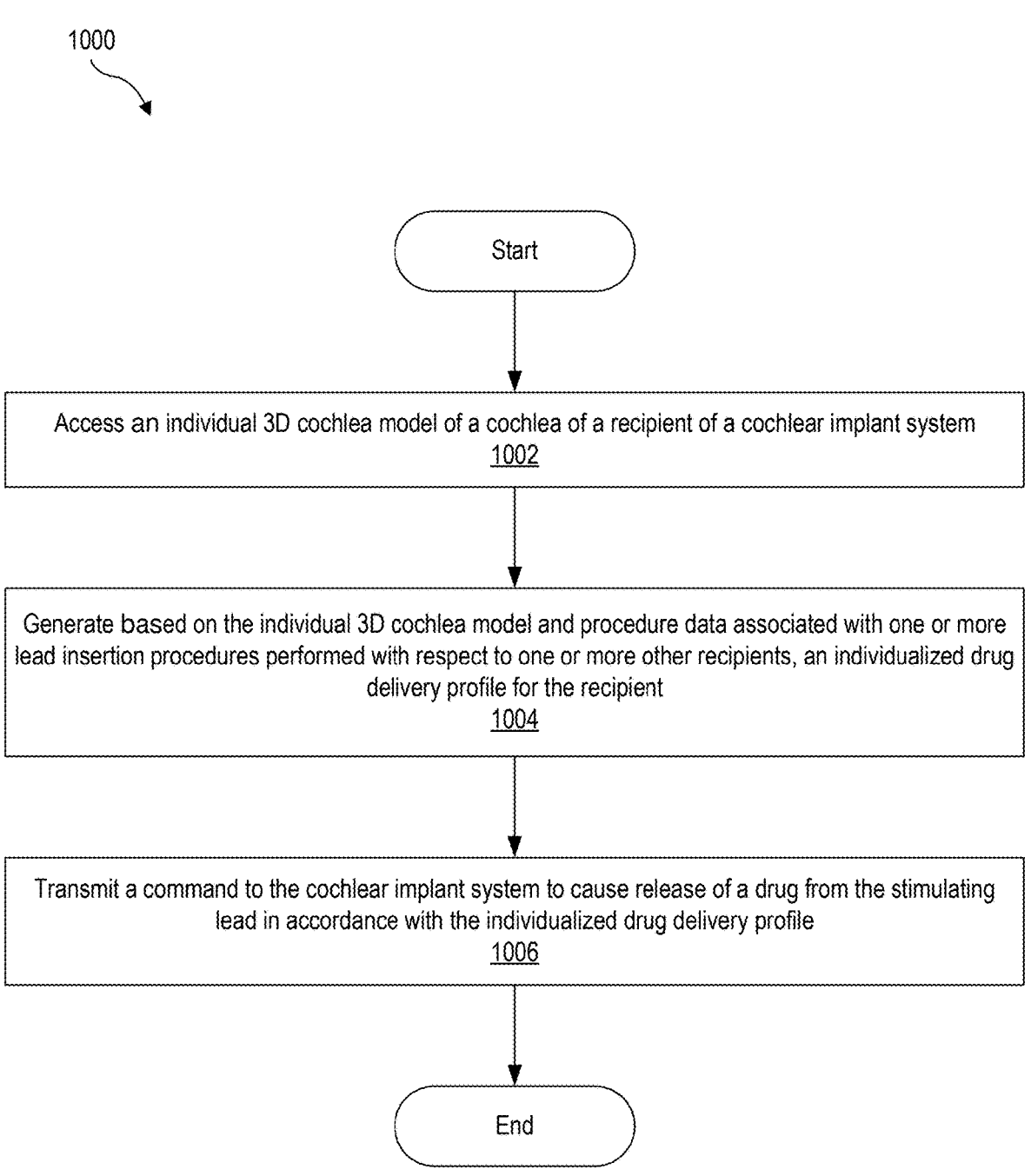
FIG. 10 shows an exemplary method according to principles described herein.

FIG. 10 illustrates an additional exemplary method 1000 for implementing an individualized drug delivery profile for a recipient of a cochlear implant system. While FIG. 10 illustrates exemplary operations according to one embodiment, other embodiments may omit, add to, reorder, and/or modify any of the operations shown in FIG. 10.

At operation 1002, a cochlear implant management system (e.g., cochlear implant management system 500) may access an individual 3D cochlea model of a cochlea of a recipient of a cochlear implant system. The cochlear implant system may include a stimulating lead that may be inserted into the cochlea during a lead insertion procedure. Operation 1002 may be performed in any of the ways described herein.

At operation 1004, the cochlear implant management system may generate, based on the individual 3D cochlea model and procedure data associated with one or more lead insertion procedures performed with respect to one or more other recipients, an individualized drug delivery profile for the recipient. Operation 1004 may be performed in any of the ways described herein.

At operation 1006, the cochlear implant management system may transmit a command to the cochlear implant system to cause release of a drug from the stimulating lead in accordance with the individualized drug delivery profile. Operation 1006 may be performed in any of the ways described herein.

In some examples, a computer program product embodied in a non-transitory computer-readable storage medium may be provided. In such examples, the non-transitory computer-readable storage medium may store computer-readable instructions in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g., a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 11:
FIG. 11 shows an exemplary computing device that may be implemented according to principles described herein.
Figure 11:
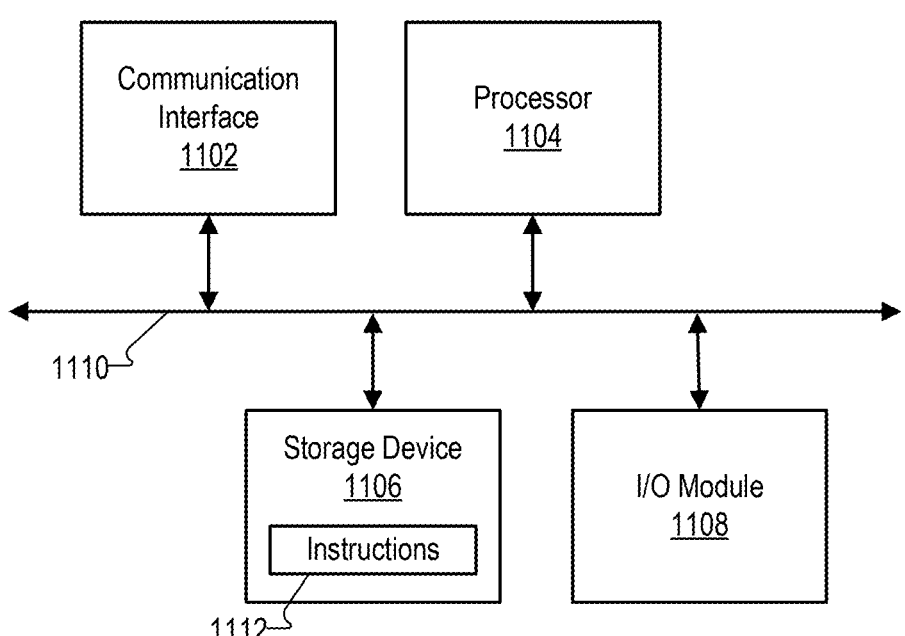

FIG. 11 illustrates an exemplary computing device 1100 that may be specifically configured to perform one or more of the processes described herein. As shown in FIG. 11, computing device 1100 may include a communication interface 1102, a processor 1104, a storage device 1106, and an input/output ("I/O") module 1108 communicatively connected one to another via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data and/or interpreting, executing, and/or directing execution of one or more of the instructions, processes, and/or operations described herein. Processor 1104 may perform operations by executing computer-executable instructions 1112 (e.g., an application, software, code, and/or other executable data instance) stored in storage device 1106.

Storage device 1106 may include one or more data storage media, devices, or configurations and may employ any type, form, and combination of data storage media and/or device. For example, storage device 1106 may include, but is not limited to, any combination of the non-volatile media and/or volatile media described herein. Electronic data, including data described herein, may be temporarily and/or permanently stored in storage device 1106. For example, data representative of computer-executable instructions 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the systems, hearing devices, computing devices, and/or other components described herein may be implemented by computing device 1100. For example, memory 112 and/or memory 502 may be implemented by storage device 1106, and processor 114 and/or processor 504 may be implemented by processor 1104.

Advantages and features of the present disclosure can be further described by the following statements:

1. A system comprising: a memory that stores instructions; and a processor communicatively coupled to the memory and configured to execute the instructions to perform a process comprising: accessing an individual three-dimensional ("3D") cochlea model of a cochlea of a recipient of a cochlear implant system that includes a stimulating lead inserted into the cochlea during a lead insertion procedure; generating, based on the individual 3D cochlea model and procedure data associated with one or more lead insertion procedures performed with respect to one or more other recipients, an individualized drug delivery profile for the recipient; and transmitting a command to the cochlear implant system to cause release of a drug from the stimulating lead in accordance with the individualized drug delivery profile.

2. The system of the preceding statement, wherein: the process further comprises performing, based on the individual 3D cochlea model, a simulation to determine an estimated position of the stimulating lead within the cochlea; and the generating of the individualized drug delivery profile is further based on the simulation.

3. The system of any of the preceding statements, wherein the performing of the simulation is further based on a type of stimulating lead inserted during the lead insertion procedure.

4. The system of any of the preceding statements, wherein: the process further comprises determining, based on the individual 3D model and post-operative scan images of the recipient, a position of the stimulating lead within the cochlea; and the generating of the individualized drug delivery profile is further based on the determining of the position of the stimulating lead within the cochlea.

5. The system of any of the preceding statements, wherein: the stimulating lead includes a plurality of stimulating portions arranged along a length of the stimulating lead; and the command to the cochlear implant system causes the drug to be released from a first portion of the stimulating lead that includes only a subset of stimulating portions included in the plurality of stimulating portions.

6. The system of any of the preceding statements, wherein the first portion of the stimulating lead is at a position within the cochlea that is subject to at least one of trauma, fibrosis, or inflammation that occur at least one of during the lead insertion procedure or after the lead insertion procedure.

7. The system of any of the preceding statements, wherein: the command to the cochlear implant system causes the drug to be released from a second portion of the stimulating lead that includes only an additional subset of stimulating portions included in the plurality of stimulating portions; and the first portion of the stimulating lead and the second portion of the stimulating lead are separated along the length of the stimulating lead by a third portion of the stimulating lead from which the drug is not released in response to the command.

8. The system of any of the preceding statements, wherein: the stimulating lead is an electrode lead that includes a plurality of electrode contacts arranged along a length of the electrode lead; and the command directs the cochlear implant system to provide electrical current by way of one or more electrode contacts included in the plurality of electrode contacts to cause release of the drug from the electrode lead.

9. The system of any of the preceding statements, wherein: the stimulating lead is an optrode lead that includes a plurality of optrodes arranged along a length of the optrode lead; and the command directs the cochlear implant system to emit light by way of one or more optrodes included in the plurality of optrodes to cause release of the drug from the optrode lead.

10. The system of any of the preceding statements, wherein the command is transmitted a predefined amount of time subsequent to completion of the lead insertion procedure.

11. A computer program product embodied on a non-transitory computer readable medium and comprising computer instructions for: accessing an individual three-dimensional ("3D") cochlea model of a cochlea of a recipient of a cochlear implant system that includes a stimulating lead inserted into the cochlea during a lead insertion procedure; generating, based on the individual 3D cochlea model and procedure data associated with one or more lead insertion procedures performed with respect to one or more other recipients, an individualized drug delivery profile for the recipient; and transmitting a command to the cochlear implant system to cause release of a drug from the stimulating lead in accordance with the individualized drug delivery profile.

12. The computer program product of the preceding statement, wherein: the stimulating lead includes a plurality of stimulating portions arranged along a length of the stimulating lead; and the command to the cochlear implant system causes the drug to be released from a first portion of the stimulating lead that includes only a subset of stimulating portions included in the plurality of stimulating portions.

13. The computer program product of any of the preceding statements, wherein the first portion of the stimulating lead is at a position within the cochlea that is subject to at least one of trauma, fibrosis, or inflammation that occur at least one of during the lead insertion procedure or after the lead insertion procedure.

14. The computer program product of any of the preceding statements, wherein: the command to the cochlear implant system causes the drug to be released from a second portion of the stimulating lead that includes only an additional subset of stimulating portions included in the plurality of stimulating portions; and the first portion of the stimulating lead and the second portion of the stimulating lead are separated along the length of the stimulating lead by a third portion of the stimulating lead from which the drug is not released in response to the command.

15. A method comprising: accessing, by a cochlear implant management system, an individual three-dimensional ("3D") cochlea model of a cochlea of a recipient of a cochlear implant system that includes a stimulating lead inserted into the cochlea during a lead insertion procedure; generating, by the cochlear implant management system and based on the individual 3D cochlea model and procedure data associated with one or more lead insertion procedures performed with respect to one or more other recipients, an individualized drug delivery profile for the recipient; and transmitting, by the cochlear implant management system, a command to the cochlear implant system to cause release of a drug from the stimulating lead in accordance with the individualized drug delivery profile.

16. The method of the preceding statement, further comprising performing, by the cochlear implant management system and based on the individual 3D cochlea model, a simulation to determine an estimated position of the stimulating lead within the cochlea, wherein the generating of the individualized drug delivery profile is further based on the simulation.

17. The method of any of the preceding statements, wherein the performing of the simulation is further based on a type of stimulation lead inserted during the lead insertion procedure.

18. The method of any of the preceding statements, further comprising determining, by the cochlear implant management system and based on the individual 3D model and post-operative scan images of the recipient, a position of the stimulating lead within the cochlea, wherein the generating of the individualized drug delivery profile is further based on the determining of the position of the stimulating lead within the cochlea.

19. The method of any of the preceding statements, wherein the command is transmitted a predefined amount of time subsequent to completion of the lead insertion procedure.

20. The method of any of the preceding statements, wherein the command causes the drug to be controllably released to a portion of the cochlea that is subject to at least one of trauma, fibrosis, or inflammation that occur at least one of during the lead insertion procedure or after the lead insertion procedure.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory that stores instructions; and
a processor communicatively coupled to the memory and configured to execute the instructions to perform a process comprising:
accessing an individual three-dimensional ("3D") cochlea model of a cochlea of a recipient of a cochlear implant system that includes a stimulating lead inserted into the cochlea during a lead insertion procedure;
generating, based on the individual 3D cochlea model and procedure data associated with one or more lead insertion procedures performed with respect to one or more other recipients, an individualized drug delivery profile for the recipient; and
transmitting a command to a stimulating portion of the stimulating lead of the cochlear implant system to cause controllable release of a drug from the stimulating lead inserted within the recipient in accordance with the individualized drug delivery profile for the recipient.

2. The system of claim 1, wherein:
the process further comprises performing, based on the individual 3D cochlea model, a simulation to determine an estimated position of the stimulating lead within the cochlea; and
the generating of the individualized drug delivery profile is further based on the simulation.

3. The system of claim 2, wherein the performing of the simulation is further based on a type of stimulating lead inserted during the lead insertion procedure.

4. The system of claim 1, wherein:
the process further comprises determining, based on the individual 3D model and post-operative scan images of the recipient, a position of the stimulating lead within the cochlea; and
the generating of the individualized drug delivery profile is further based on the determining of the position of the stimulating lead within the cochlea.

5. The system of claim 1, wherein:
the stimulating lead includes a plurality of stimulating portions arranged along a length of the stimulating lead; and
the command to the stimulating portion of the stimulating lead of the cochlear implant system causes the drug to be released from a first portion of the stimulating lead that includes only a subset of stimulating portions included in the plurality of stimulating portions.

6. The system of claim 5, wherein the first portion of the stimulating lead is at a position within the cochlea that is subject to at least one of trauma, fibrosis, or inflammation that occur at least one of during the lead insertion procedure or after the lead insertion procedure.

7. The system of claim 5, wherein:

the process further comprises transmitting an additional command to an additional stimulating portion of the stimulating lead;

the additional command to the additional stimulating portion of the stimulating lead of the cochlear implant system causes the drug to be released from a second portion of the stimulating lead that includes only an additional subset of stimulating portions included in the plurality of stimulating portions; and the first portion of the stimulating lead and the second portion of the stimulating lead are separated along the length of the stimulating lead by a third portion of the stimulating lead from which the drug is not released in response to the additional command.

8. The system of claim 1, wherein:

the stimulating lead is an electrode lead that includes a plurality of electrode contacts arranged along a length of the electrode lead; and the command directs the cochlear implant system to provide electrical current by way of one or more electrode contacts included in the plurality of electrode contacts to cause release of the drug from the electrode lead.

9. The system of claim 1, wherein:

the stimulating lead is an optrode lead that includes a plurality of optrodes arranged along a length of the optrode lead; and the command directs the cochlear implant system to emit light by way of one or more optrodes included in the plurality of optrodes to cause release of the drug from the optrode lead.

10. The system of claim 1, wherein the command is transmitted a predefined amount of time subsequent to completion of the lead insertion procedure.

11. A computer program product embodied on a non-transitory computer readable medium and comprising computer instructions for:

accessing an individual three-dimensional ("3D") cochlea model of a cochlea of a recipient of a cochlear implant system that includes a stimulating lead inserted into the cochlea during a lead insertion procedure;

generating, based on the individual 3D cochlea model and procedure data associated with one or more lead insertion procedures performed with respect to one or more other recipients, an individualized drug delivery profile for the recipient; and transmitting a command to the cochlear implant system to cause release of a drug from the stimulating lead inserted within the recipient in accordance with the individualized drug delivery profile for the recipient.

12. The computer program product of claim 11, wherein:

the stimulating lead includes a plurality of stimulating portions arranged along a length of the stimulating lead; and the command to the stimulating portion of the stimulating lead of the cochlear implant system causes the drug to be released from a first portion of the stimulating lead that includes only a subset of stimulating portions included in the plurality of stimulating portions.

13. The computer program product of claim 12, wherein the first portion of the stimulating lead is at a position within the cochlea that is subject to at least one of trauma, fibrosis, or inflammation that occur at least one of during the lead insertion procedure or after the lead insertion procedure.

14. The computer program product of claim 12, wherein:

the instructions are further for transmitting an additional command to an additional stimulating portion of the stimulating lead;

the additional command to the additional stimulating portion of the stimulating lead of the cochlear implant system causes the drug to be released from a second portion of the stimulating lead that includes only an additional subset of stimulating portions included in the plurality of stimulating portions; and the first portion of the stimulating lead and the second portion of the stimulating lead are separated along the length of the stimulating lead by a third portion of the stimulating lead from which the drug is not released in response to the additional command.

15. A method comprising:

accessing, by a cochlear implant management system, an individual three-dimensional ("3D") cochlea model of a cochlea of a recipient of a cochlear implant system that includes a stimulating lead inserted into the cochlea during a lead insertion procedure;

generating, by the cochlear implant management system and based on the individual 3D cochlea model and procedure data associated with one or more lead insertion procedures performed with respect to one or more other recipients, an individualized drug delivery profile for the recipient; and transmitting, by the cochlear implant management system, a command to the cochlear implant system to cause release of a drug from the stimulating lead inserted within the recipient in accordance with the individualized drug delivery profile for the recipient.

16. The method of claim 15, further comprising performing, by the cochlear implant management system and based on the individual 3D cochlea model, a simulation to determine an estimated position of the stimulating lead within the cochlea, wherein the generating of the individualized drug delivery profile is further based on the simulation.

17. The method of claim 16, wherein the performing of the simulation is further based on a type of stimulating lead inserted during the lead insertion procedure.

18. The method of claim 15, further comprising determining, by the cochlear implant management system and based on the individual 3D model and post-operative scan images of the recipient, a position of the stimulating lead within the cochlea, wherein the generating of the individualized drug delivery profile is further based on the determining of the position of the stimulating lead within the cochlea.

19. The method of claim 15, wherein the command is transmitted a predefined amount of time subsequent to completion of the lead insertion procedure.

20. The method of claim 15, wherein the command causes the drug to be controllably released to a portion of the cochlea that is subject to at least one of trauma, fibrosis, or inflammation that occur at least one of during the lead insertion procedure or after the lead insertion procedure.

* * * * *